(12) United States Patent
Chi et al.

(10) Patent No.: US 7,704,388 B2
(45) Date of Patent: Apr. 27, 2010

(54) REUSABLE LIQUID CHROMATOGRAPHIC COLUMNS

(75) Inventors: Yawu Chi, Sharon, MA (US); Lixin Cao, Princeton, NJ (US); Ying Xu, Edison, NJ (US)

(73) Assignee: Luknova, Inc, Princeton, NJ (US)

( * ) Notice: Subject to any disclaimer, the term of this patent is extended or adjusted under 35 U.S.C. 154(b) by 737 days.

(21) Appl. No.: 11/307,312

(22) Filed: Jan. 31, 2006

(65) Prior Publication Data

US 2007/0175809 A1 Aug. 2, 2007

(51) Int. Cl.
 *B01D 15/08* (2006.01)
(52) U.S. Cl. .................... 210/198.2; 210/232; 210/282; 210/656
(58) Field of Classification Search ............... 210/198.2, 210/635, 656, 232, 238, 282; 96/101, 105, 96/106; 95/82
See application file for complete search history.

(56) References Cited

U.S. PATENT DOCUMENTS

| | | | | |
|---|---|---|---|---|
| 3,483,986 A * | 12/1969 | Wright | .................... | 210/198.2 |
| 4,565,632 A * | 1/1986 | Hatch et al. | .................. | 210/656 |
| 4,876,005 A * | 10/1989 | America | .................. | 210/198.2 |
| 5,342,515 A * | 8/1994 | Radmacher | .............. | 210/198.2 |
| 5,601,708 A | 2/1997 | Leavesley | ................ | 210/198.2 |
| 5,716,525 A * | 2/1998 | Nickerson | ................... | 210/634 |
| 6,325,929 B1 * | 12/2001 | Bassett | ....................... | 210/238 |
| 6,358,414 B1 * | 3/2002 | Maiefski | .................. | 210/198.2 |
| 6,423,220 B1 | 7/2002 | Fex | .......................... | 210/198.2 |
| 6,436,284 B1 | 8/2002 | Leavesley et al. | ........ | 210/198.2 |
| 6,458,273 B1 * | 10/2002 | Krakover et al. | ......... | 210/198.2 |
| 6,565,745 B2 | 5/2003 | Hodgin et al. | ............ | 210/198.2 |
| 6,692,556 B2 * | 2/2004 | Hayes et al. | .................. | 96/147 |
| 6,736,973 B1 * | 5/2004 | Podgornik et al. | .......... | 210/656 |
| 6,797,174 B2 | 9/2004 | Neuroth | ...................... | 210/656 |
| 6,811,688 B1 | 11/2004 | Hofmann | .................. | 210/198.2 |
| 6,949,194 B2 | 9/2005 | Hodgin et al. | .............. | 210/656 |
| 2002/0008058 A1 * | 1/2002 | Nugent | ..................... | 210/198.2 |
| 2004/0129624 A1 * | 7/2004 | Hamlin et al. | .............. | 210/315 |
| 2005/0133426 A1 * | 6/2005 | DeMarco | .................. | 210/198.2 |
| 2005/0242018 A1 * | 11/2005 | Hodgin et al. | ........... | 210/198.2 |
| 2006/0207939 A1 * | 9/2006 | Allington et al. | ........... | 210/656 |
| 2007/0163102 A1 * | 7/2007 | DeMarco | .................. | 29/525.14 |

* cited by examiner

*Primary Examiner*—Ernest G Therkorn
(74) *Attorney, Agent, or Firm*—Steven N. Fox

(57) ABSTRACT

A reusable liquid chromatographic column consists of three parts, a column body with an integral outlet port molded on one end, a sealing insert with an inlet port, and a perforated cap providing downward force to compress the sealing insert into the column body. A wedge-like seal is employed to seal the connection between the sealing insert and the column body. Two filters on both ends of the column body are used to prevent escape of packing materials from the column chamber under pressure. Hand tightening is adequate to seal the connection by screwing the perforated cap onto the column body. The column is reusable due to its simple disassembling and reassembling processes. It is also disposable due to its inexpensive fabricating materials and manufacturing process.

5 Claims, 7 Drawing Sheets

REUSABLE LIQUID CHROMATOGRAPHIC COLUMNS

BACKGROUND OF THE INVENTION

The invention relates to liquid chromatographic columns and methods of assembling and disassembling reusable, economic, and leak-free chromatographic columns.

Liquid chromatography is an analytical chromatographic technique that is based on differences in partitioning behaviors between a mobile phase and a stationary phase to separate the components in a mixture, more specifically, to separate ions or molecules dissolved in a solvent. A column is packed with the stationary phase and the mobile phase carries the mixture through it. Sample components having stronger affinity with the stationary phase spend longer time in the column and are separated from components that have weaker affinity with the stationary phase and pass through the column faster.

In pursuit of optimal separation, the chromatography system is usually operated under pressure to facilitate the flow of the mobile phase in the stationary phase. As a consequence, the columns demand effective seals to prevent the mobile phase from leaking out of the pressurized passage. An O-ring employed in some prior art methods (U.S. Pat. No. 5,601,708 and U.S. Pat. No. 6,436,284) can provide a good seal for the openings of the column, but some organic solvents used as a mobile phase in liquid chromatography can damage the O-ring after a lengthy soaking in the solvents. The methods for making commercially available disposable columns (U.S. Pat. Nos. 6,565,745 and 6,949,194) involve the use of a snap-on cap to form a sealing connection between the column body and the sealing head. This technique could lead to sealing failure under substantial pressure build-up. In addition, the use of snap-on cap with cantilever members and the ramped detents molded on the column body forms a tight interference fit, which practically makes the column solely for one-time use due to the inability in disassembling column for repeated uses. Columns made of glass (U.S. Pat. No. 6,811,688) cannot withstand a pressurized system and cost more than plastic columns. Other prior art technique (U.S. Pat. No. 6,797,174) requires a complicated process involving six separate pieces and one spacer ring. A low-pressure liquid chromatographic cartridge is provided with a resilient fluid tight seal (US Patent Application 2005/0247632), but the rotation resulted from threading the cap onto the cartridge container could cause seal failure and the cartridge is not reusable.

All these prior art techniques have the drawbacks of high cost for column assembly, seal failure, or one-time use. It is the object of this invention to provide reusable, economic, and leak-proof liquid chromatographic columns for the separation and purification of organic compounds.

SUMMARY OF THE INVENTION

The invention is aimed at providing reusable, economic and leak-proof liquid chromatographic columns. It is still aimed at providing a simple, but reliable process to assemble and disassemble the columns. In one aspect, the columns can be reusable since the assembly and disassembly processes are easy to fulfill without assistance from special devices or machines. Conventional tools, such as pliers, wrenches, and tweezers, are adequate to disassemble and assemble the columns. In another aspect, the columns are also disposable due to its inexpensive materials and simple assembly process.

The column includes three separate parts, a cylindrical body with one end having one port molded as a single piece to the body and the other end with an opening for loading the packing material and sealing, a sealing insert molded with another port directed toward the body chamber, and a perforated cap used to force the sealing insert into the column body by use of hand-tightening. At the both ends of the packing material loaded in the column chamber, two filters are employed to prevent the packing material from entering the ports.

In the preferred embodiment, a wedge-like seal is adopted to the connection between the column body with a tapered rim on the inner wall and the sealing insert with a conical circumference. The outer wall on the opening portion of the column body is molded with male threads for the perforated cap comprising female threads. The sealing insert, along with the perforated cap around it, is placed into the column body. By turning the cap onto the column base, the perforated cap provides straight downward force to push the sealing insert into the column body to form a compression type fitting. The perforated cap has small ridges on the outer wall to aid in gripping and hand-tightening with ease.

One of the advantages and features of this invention is the column designed for repeated uses. Although the used column is disposable, it can afford multiple uses with appropriate disassembling and reassembling processes. The used column is readily disassembled by unscrewing the perforated cap, pulling out the sealing insert, and then removing filters and the packing material. After reloading with new packing material and filters into the used column body, the used sealing insert and perforated cap are reassembled onto the column body to form a new column with tight seal. A column in this embodiment can be reused up to ten times, preferably two to three times with replacement of new packing material and filters each time. The number of using times is subject to the integrity of the sealing interface between the sealing insert and the column body. A smooth surface free of cracks or niches is indispensable for the column reassembly. The invented liquid-chromatographic columns can sustain relatively high pressure up to 180 psi.

The column may also be disposable thanks to its inexpensive fabricating material, such as polyethylene, polypropylene, and its economic assembling process. Packing materials include silica, silica gel, alumina, regenerated silica, regenerated silica gel, regenerated alumina, and the like. Hand-tightening without or with slight assistance from wrenches or pliers is sufficient to provide reliable seal under substantial internal pressure. Other advantages of this invention will be described in the preferred embodiment thereof and from the claims.

DESCRIPTION OF THE DRAWINGS

For the purpose of easy understanding the advantages this invention brings, the following seven drawings are used to explicitly describe the column features and the assembling and disassembling processes.

DESCRIPTION OF THE PREFERRED EMBODIMENTS

Figure 1:
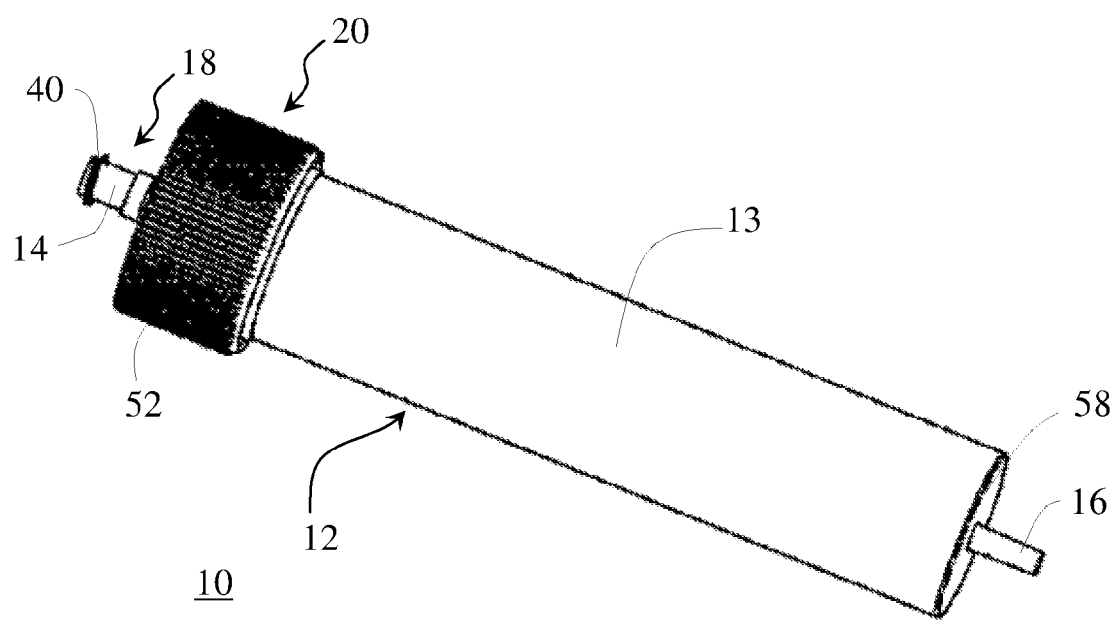
FIG. 1 is a perspective view of the whole column based on this invention.

FIG. 1 shows a perspective view of the whole column in this embodiment. The chromatographic column 10 with a cylindrical structure has a sealing insert 18 with a molded inlet port 14, a perforated cap 20, and a column body 12 with a molded outlet port 16. The packing material is loaded inside the column chamber 13. In the operation procedure, the inlet port 14 is connected to a source where the mobile phase flows into the column 10. The mobile phase carries mixture from the inlet port 14 to outlet port 16 through the packing material in which components are separated due to different retention times caused by the difference in affinity of each component to the packing material. The outlet port delivers the separated components to a detecting device to identify or quantify each component, which is finally collected in containers. The size of the column 10 varies with the amount of separated samples.

Figure 2:
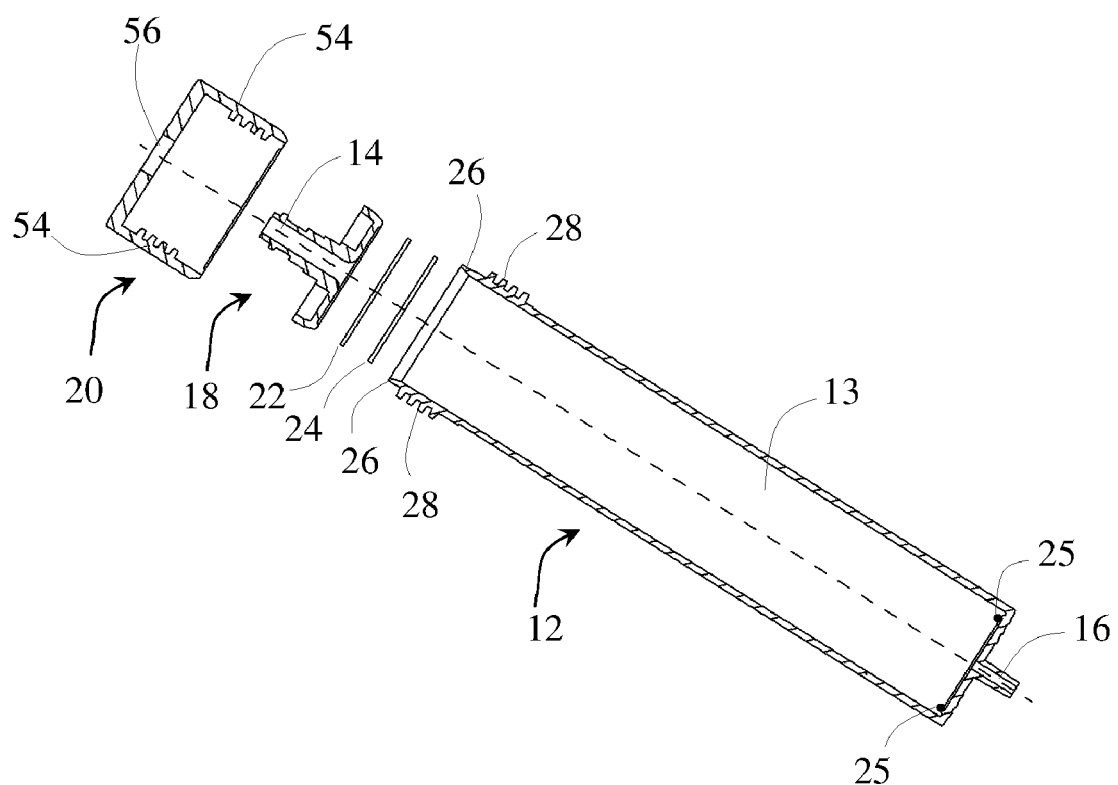
FIG. 2 is an exploded cross-sectional view of the column of FIG. 1.

Referring to FIG. 2, it is seen that the column 10 has five pieces in sequence: a perforated cap 20 with an opening 56, a sealing insert 18 with an inlet port 14, an inlet filter 22, an outlet filter 24, and a column body 12 molded with an outlet port 16. The cylindrical chamber 13 is for filling the packing material, such as silica gel. Two filters 22 and 24, porous frit, are placed on the two ends of the column chamber 13 to avoid the leaks of the packing material from the column body 12. The inlet port 14 is integrally molded on the sealing insert 18, which is placed into the open end of the column body in the assembling process. A perforated cap 20 with female threads 54 is used to fix the sealing insert 18 into the column body 12 with a sealing connection.

Figure 3:
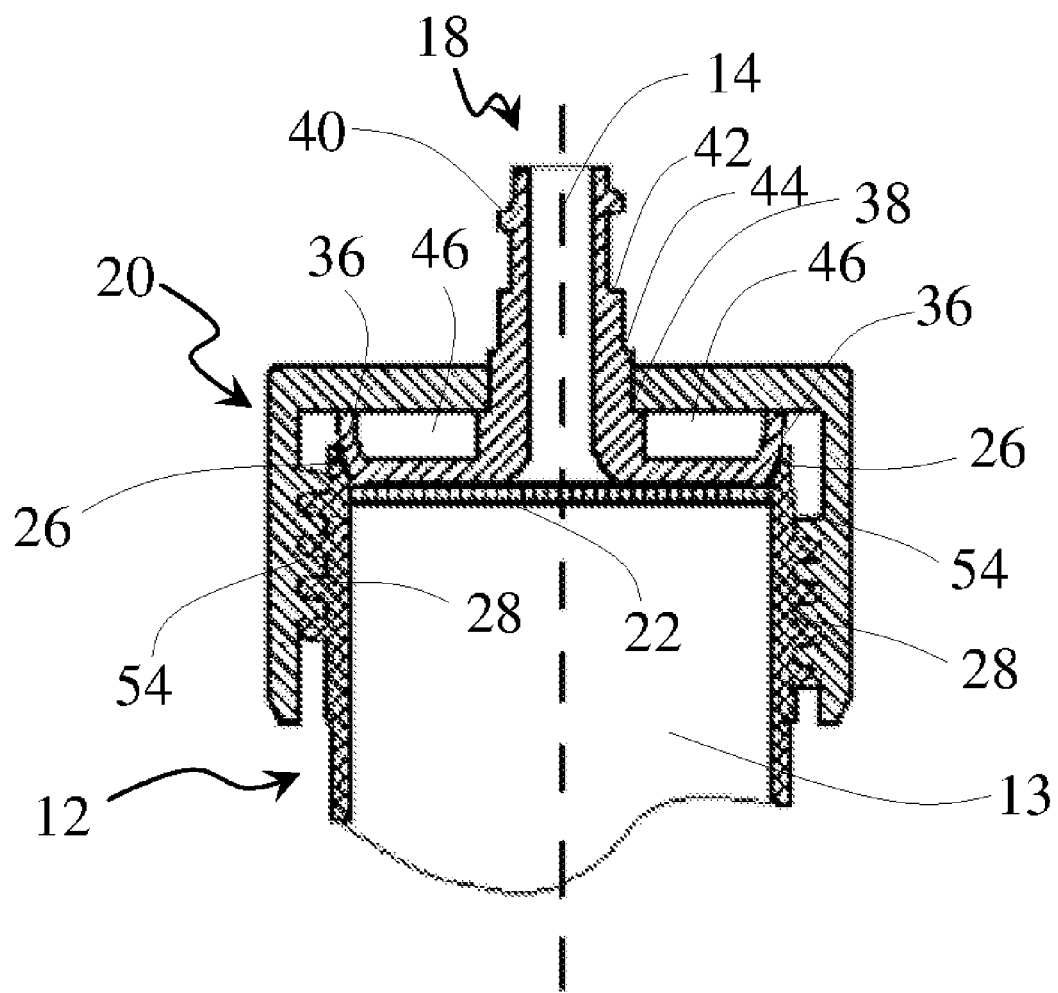
FIG. 3 is a fragmentary sectional view of the sealing part.

The sealing connection of the apparatus is shown in FIG. 3. The wedge-like seal is used to form a tight seal at the inlet end. The inlet opening of the column body 12 consists of a tapered end 26, which receives a slope 36 on the sealing insert 18 to form the sealing surface. The perforated cap 20 is placed onto the sealing insert 18 to provide downward force to push the sealing insert 18 into the column body 12 by screwing down the perforated cap onto the column body. In this sealing connection, the perforated cap 20 with female threads 54 plays a role as a nut with female threads and the column body 12 is like a hollow bolt with male threads 28 on the outer wall. The sealing insert 18 is forced to move linearly downward into the column body 12 without tangential rotating movement. A compression-type fitting is formed between the slope 36 of the sealing insert 18 and the tapered rim 26. The use of threads in the connection allows easy disconnection of the perforated cap 20, the sealing insert 18, and the column body 12 without damaging the sealing interface. The outer diameter of the step 44 of the sealing insert 20 is sized to fit within the perforation opening 56 of the perforated cap 20 with minimum radial clearance of 0.01 mm to 10 mm between the two. The clearance leads to easy operation and avoids tangential rotating movement between the sealing insert 18 and the tapered end 26 during the cyclic operation of assembly, disassembly, and reassembly. The design aimed at easy disassembly and reassembly of the column provides a base for reusing the column with multiple times.

Figure 4:
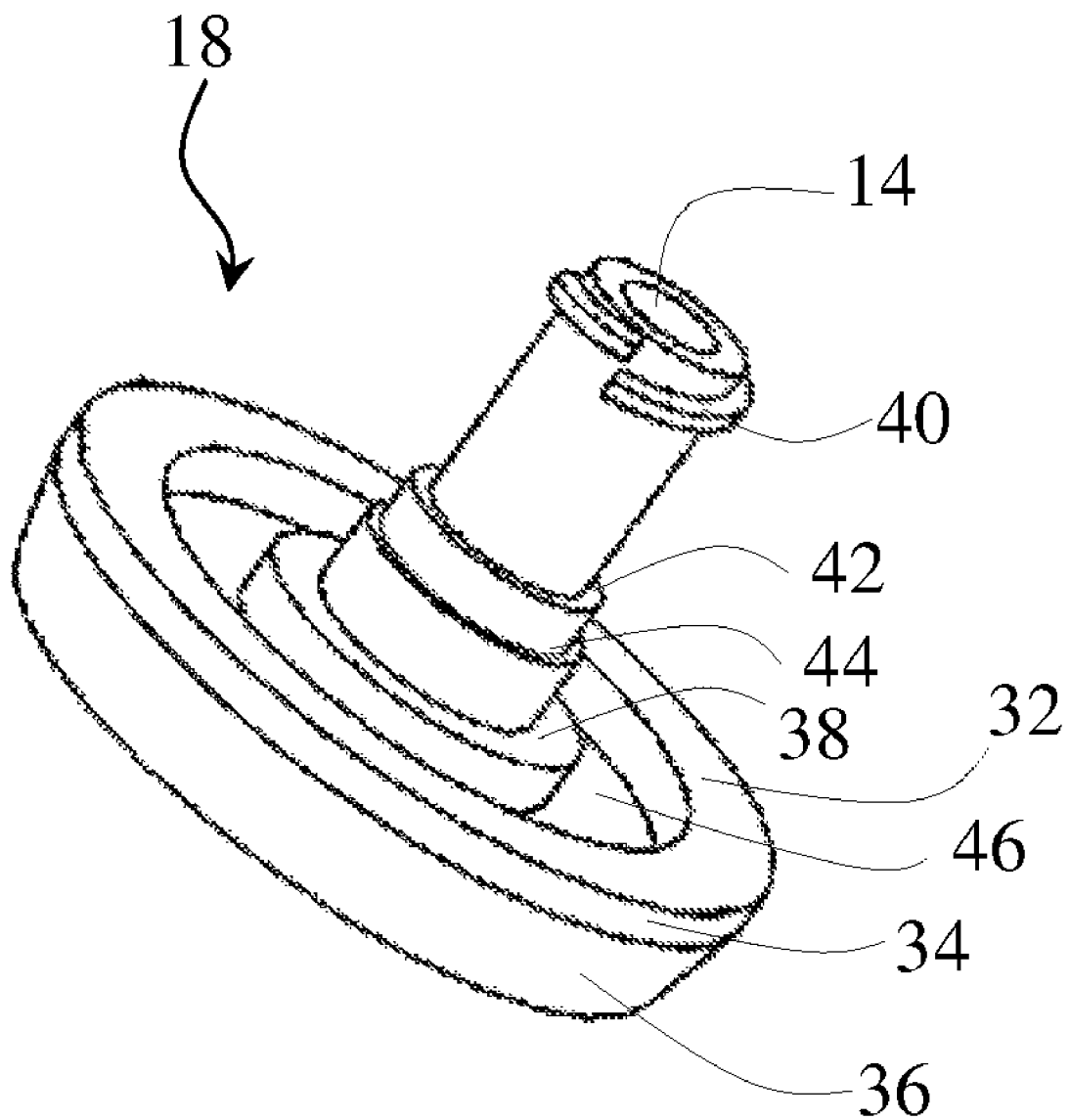
FIG. 4 is a perspective view of the sealing insert (Type I)
Figure 5:
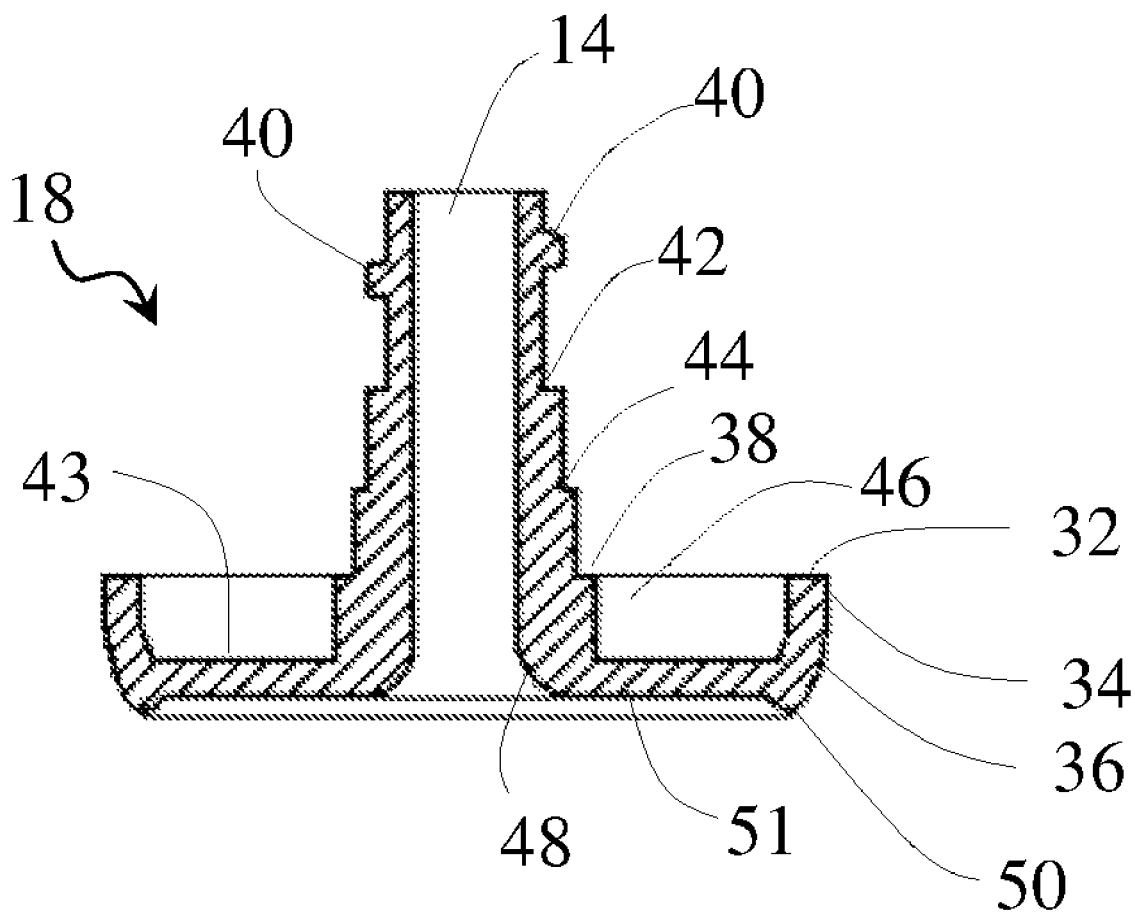
FIG. 5 is a cross-sectional view of the sealing insert of FIG. 4.

FIG. 4 shows a conventional design (Type-I) for the insert 18. The inlet port 14 has a female luer fitting with partial male threads 40 to connect to a source where the mobile phase flows through. Finger-tightening is adequate to connect the inlet port to the source of the mobile phase by turning the fitting on. Referring to FIG. 5, the radius of the circumferential stair 32 is extended to be a little larger than the inner radius of the opening of the column body 12 in avoidance of the whole sealing insert 18 entering the column body 12. A side slope 36 with an angel from 5 to 75°, preferably from 10 to 50°, mating the surface of the tapered end 26 allows the sealing insert 18 to slide into the column body 12. Three stairs 38, 42 and 44 are employed to reinforce the hardness and mechanical strength of the inlet port. Although the stairs with other numbers of more than three or less than one (no stair) can be used, two to three stairs are preferred in the invention for repeated uses. The height of the stair 38 is equal to the height of the circumferential stair 32 in order to receive even downward force in the center and on the edge of the sealing insert 18. The use of the recess 46 between stair 38 and 32 is aimed at saving materials and avoiding the insert deformation caused by thick layer in the molding process.

As shown in FIG. 5, a conical shape 48, which is open toward the inlet filter 22 at the end the inlet passage, is designed to allow even dispersion of fluid cross the filter 22 and the packing materials in the column body 12. The sealing insert 18 has an additional circular protrusion 50 on the rim of the insert bottom 51. The protrusion with a height of 1.5 mm (e.g. 0.5 to 5 mm, preferably 1 to 3 mm) has a 75° angel (e.g. 30 to 150°, preferably 60 to 120°) in section and protrudes downward from the surface 51. After compressed downward, the protrusion 50 can dig into the filter 22, which is tightly against the walls of the column body 12 to stop the movement of packing materials under pressure, to form a seal in case that any defect fitting between the filter 22 and the column wall cause the leaks of the packing material. Accordingly, another protrusion 25 with the size equal to the protrusion 50 is positioned against the filter 24 at the outlet end to prevent leaks of the packing material to the outlet port 16. The disk-shaped filters 22 and 24 are made of porous polymer with elasticity for receiving pressing from the protrusions 50 and 25, respectively.

Figure 6:
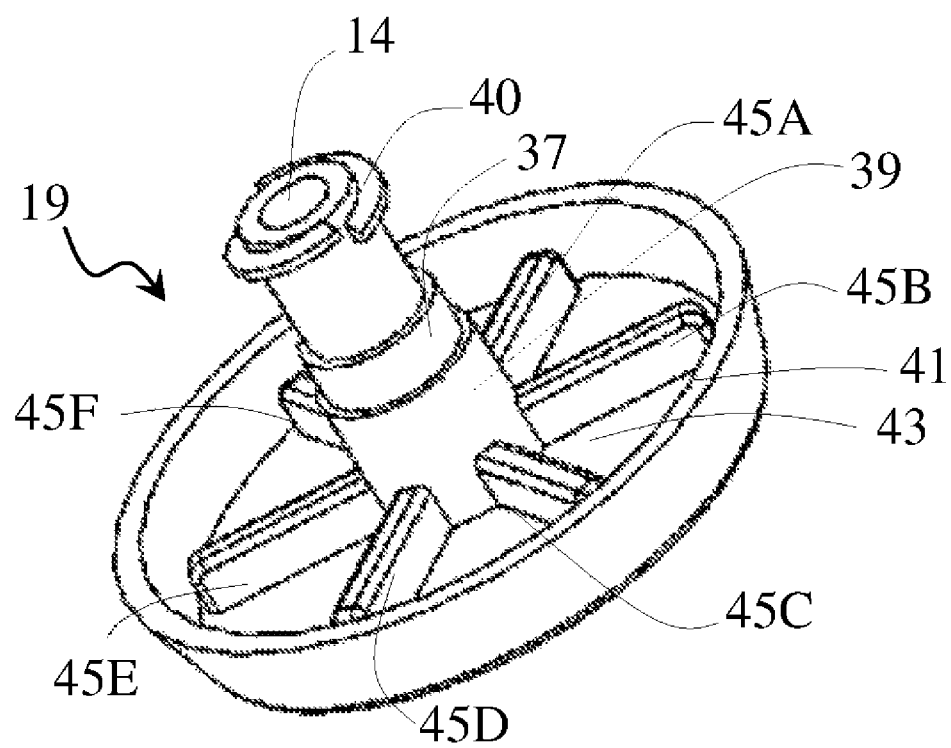
FIG. 6 is a perspective view of the sealing insert (Type II)

An alternative design (Type-II) for the sealing insert is shown in FIG. 6. The sealing insert 19 has radial spokes 45A-45F with a number of 6 (e.g. 2 to 16, preferably 4 to 12). The spokes 45A-45F molded on the bottom 43 of the sealing insert 19 are used to increase the mechanical strength of the bottom 43 and enable the bottom to withstand substantial internal pressure. The spoke height is lower than that of the circumferential step 41. The spokes 45A-45F are extended from the stair 39 outwardly, but not reach to the wall of the circumferential step 41. The space between the end of each spoke and the wall is intended to make the sealing slope receive the even force from the tapered rim 26. Stairs 37 and 39 are used to reinforce the mechanical strength of the inset port 14. This spoke-molded insert is preferably designed for a big size column, which has a large contact surface between the sealing insert and the filter 22. The bottom surface 43 integrated with spokes of the sealing insert 19 can prevent deformation under high internal pressure. The radial spokes can also be employed to increase the mechanical strength of the bottom 58 at the outlet of the column body 12 for the sake of high internal pressure tolerance.

Figure 7:
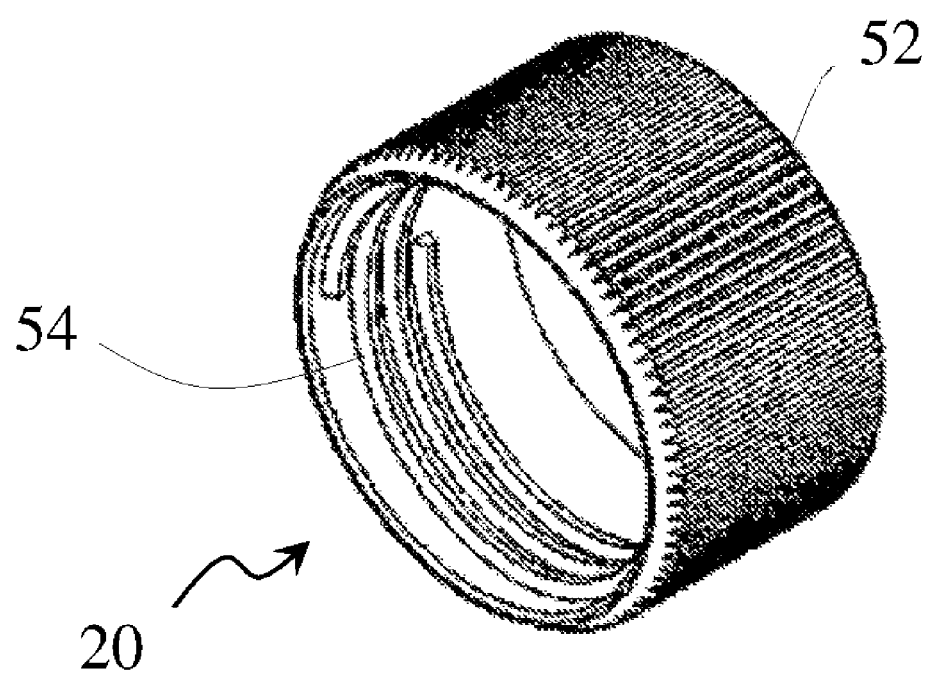
FIG. 7 is a perspective view of the perforated cap.

The compressive force applied to pushing the sealing insert 18 downward is provided from the perforated cap 20 by screwing it onto the column body 12. FIG. 7 shows the perspective view of the perforated cap 20, which functions as a nut with female threads 54. The knurls 52, regular small ridges on the outer surface of the perforated cap 20, assist to prevent slipping while the connection is tightened by hands through gripping the perforated cap 20. Referring to the cross-sectional view of the column 10 in FIG. 2, female threads 54 along with male threads 28 on the outer wall of the column body 12 can be clockwise or counter-clockwise. A perforation 56 sized between the diameters of the stair 44 and the stair 38 is formed on the top of the cap 20 to ensure that the downward force is evenly scattered on the stairs 32 and 38 of the insert 18. The connection with separate sealing insert 18 and perforated cap 20 provides only straight linear movement between the slope 36 and the tapered end 26 instead of tangential movement, which can cause abrasion and defects at the sealing interface and eventually give rise to a failed seal.

In the packing process of a chromatographic column, the filter 24 with the diameter equal to the bottom size of the column body 12 is firmly placed against the protrusion 25. The packing materials are introduced to the column chamber 13 with the assistance of vacuum hooked to the outlet port, or just by vibrating the column body 12 to ensure the packing materials closely packed inside the column chamber. Any void volume in the packing materials should be prohibited since it can lead to poor separation efficiency. After the packing material nearly reaches to the tapered end 26, the inlet filter 22 is placed on the top of the packing material layer. The sealing insert 18 is then inserted into the tapered end 26. Once the perforated cap 20 is aligned onto the sealing insert 18, the connection can be firmly formed by turning the perforated cap 20 onto the column body 12. A wrench or a pair of pliers may be applicable to aiding tightening, but hand tightening is adequate to assemble the column with tight seal.

The column allows a number of repeated uses since it can be easily disassembled and reassembled with hands. After the packing material in the used column is dry, the perforated cap 20 is readily unscrewed from the column body 12. The filters 22 and 24, as well as the packing material, are then removed from the column chamber 13. Three parts including the perforated cap 20, the sealing insert 18, and the column body 12, can be cleaned with organic solvents for the next use. With replacement of the packing material and two filters, a new column can be easily reassembled according to the assembling process described above. During the assembling and disassembling process, the contact surfaces of the tapered end 26 and the slope 36 should be kept clean, smooth, and free of any cracks or niches. The column can be used up to ten times with care of three reusable parts, the perforated cap 20, the sealing insert 18, and the column body 12.

In this design, the sealing connection consisting of the sealing insert 18 and the perforated cap 20 performs as an inlet end, as described above. However, in the preferred embodiment, the inlet port 14 and outlet port 16 can switch positions if the female luer fitting with partial male threads 40 is molded on the column end 16. As a consequence, the sealing connection would be on the outlet end. The mobile phase would flow into the column through the molded end and flow out of the column through the sealing connection end. Indeed, such an upside-down design would enhance the column resistance against leaks under a pressurized system since the outlet pressure is always lower than the inlet pressure. The preferred embodiments and illustrative details set forth should merely be regarded as descriptive disclosure. Various other changes and additions in the form and detail thereof may be made therein without departing from the spirit and scope of the invention.

In one embodiment, the device comprises a one-piece reusable plastic tubular body comprising a first open end having an inside diameter ID1. The body further comprises external threads disposed about the first open end. The body further comprises tapered rim disposed at the first open end.

The device further comprises a sealing insert comprising a stem extending upward from the base. The stem comprises first and second annular stairs, and an inlet port. The first annular stair has an outside diameter OD1. The second annular stair has an outside diameter OD2. The outside diameter OD1 of the first annular stair is larger than the outside diameter OD2 of the second annular stair. The stem further comprises a third annular stair disposed above the second annular stair. The third annular stair has an outside diameter OD3. The outside diameter OD2 of the second annular stair is larger than the outside diameter OD3 of the third annular stair. The first annular stair has a height H1 relative to the top surface of the base. The annular wall surrounds the first annular stair of the stem. The annular wall is substantially spaced apart from the first annular stair to form an annular recessed portion with the top surface. The annular wall comprises an upper annular end, an annular sloped surface, and a lower annular protrusion. The upper annular end of the annular wall has a height H2 relative to the top surface of the base. The height H1 of the first annular stair is equal to the height H2 of the upper annular end of the annular wall. The sealing insert further comprises an annular wall disposed at the perimeter of the base. The upper annular end of the annular wall has an outside diameter OD4 that is larger than the inside diameter ID1 of the first open end of the tubular body.

The device further comprises a one-piece reusable plastic cap comprising a top wall, a central opening disposed in the top wall, and an annular sidewall having internal threads removably engaged with the external threads of the tubular body. The inlet port of the stem passes that the central opening and extends outward of the top wall of the cap. The central opening has an inside diameter ID2. The inside diameter ID2 of central opening is less than the outside diameter OD1 of the first annular stair.

What is claimed is:
1. A reusable chromatographic device comprising:
   a one-piece reusable plastic tubular body comprising a first open end having an inside diameter ID1; said body further comprises external threads disposed about said first open end; said body further comprises a tapered rim disposed at said first open end;
   a one-piece reusable plastic sealing insert comprising a circular base having a perimeter portion; said sealing insert further comprising substantially planar top and bottom surfaces; said sealing insert further comprising a stem extending upward from said base; said stem comprises first and second annular stairs, and an inlet port; said first annular stair has an outside diameter OD1; said second annular stair has an outside diameter OD2; said outside diameter OD1 of said first annular stair is larger than said outside diameter OD2 of said second annular stair; said first annular stair bus a height H1 relative to said top surface of said base; said sealing insert further comprises an annular wall disposed at said perimeter of said base; said annular wall surrounds said first annular stair of said stem; said annular wall is substantially spaced apart from said first annular stair to form an annular recessed portion; said annular wall comprises an upper annular end, an annular sloped surface, and a lower annular protrusion; said upper annular end of said annular wall has a height H2 relative to said top surface of said base; said height H1 of said first annular stair is equal to said height H2 of said upper annular end of said annular wall; said upper annular end of said annular wall has an outside diameter OD4 that is larger than said ID1 of said first open end of said tubular body;
   a one-piece reusable plastic cap comprising a top wall, a central opening disposed in said top wall, and an annular sidewall having internal threads removably engaged with said external threads of said tubular body; said inlet port of said stem passes thru said central opening and extends outward of said top wall of said cap; said central opening has an inside diameter ID2; said inside diameter ID2 of central opening is less than said outside diameter OD1 of said first annular stair; and
   rotation of said cap causes said top wall of said cap to apply a straight downward force upon said upper annular end and said first annular stair of said stem, respectively, of said sealing insert; and said rotation of said cap further causes said annular sloped surface of said sealing insert to form a seal with said tapered rim of said first open end of said tubular body.

2. The device of claim 1, wherein said stem further comprises a third annular stair disposed above said second annular stair; said third annular stair has outside diameter OD3; said outside diameter OD2 of said second annular stair is lamer than said outside diameter OD3 of said third annular stair.

3. The device of claim 2, wherein said annular sloped surface has an angle in the range of 10 to 50 degrees.

4. The device of claim 3, wherein said lower annular protrusion of said annular wall has a height in the range of 1 mm to 3 mm relative to said bottom surface of said base.

5. The device of claim 4, what said lower annular protrusion of said annular wall has an angle in the range of 60 to 120 degrees.

* * * * *